(12) United States Patent
DeLand

(10) Patent No.: US 9,041,531 B1
(45) Date of Patent: May 26, 2015

(54) IDENTIFYING THE PRESENCE OF AN INDIVIDUAL NEAR MEDICAL RADIATION EMITTING EQUIPMENT

(71) Applicant: Maitland M. DeLand, Lafayette, LA (US)

(72) Inventor: Maitland M. DeLand, Lafayette, LA (US)

( * ) Notice: Subject to any disclaimer, the term of this patent is extended or adjusted under 35 U.S.C. 154(b) by 320 days.

(21) Appl. No.: 13/742,739

(22) Filed: Jan. 16, 2013

(51) Int. Cl.
| G08B 1/08 | (2006.01) |
| G08B 26/00 | (2006.01) |
| H04Q 1/30 | (2006.01) |
| G08B 19/00 | (2006.01) |
| G08B 23/00 | (2006.01) |
| A61B 5/00 | (2006.01) |
| H01J 35/16 | (2006.01) |
| G21F 3/02 | (2006.01) |
| G05B 1/01 | (2006.01) |

(52) U.S. Cl.
CPC .................. *G05B 1/01* (2013.01)

(58) Field of Classification Search
USPC .................. 340/539.12, 518, 532, 522, 573.1; 600/310; 378/203; 250/516.1
See application file for complete search history.

(56) References Cited

U.S. PATENT DOCUMENTS

2006/0250254 A1 11/2006 Harris et al.

*Primary Examiner* — George Bugg
*Assistant Examiner* — Munear Akki
(74) *Attorney, Agent, or Firm* — Eric L. Sophir; Dentons US LLP

(57) ABSTRACT

Systems and methods are disclosed herein to a radiation safety system comprising radiation emitting medical equipment; a radiation safety system controller connected to the radiation emitting medical equipment through a first communication means configured to determine a number of people within a radiation room housing the radiation emitting medical equipment and prevent the radiation emitting medical equipment from performing radiation emitting functions if the radiation safety system controller determines that more people than a maximum allowed number of people are presently in the radiation room; and a scanner connected to the radiation safety controller through a second communication means configured to detect people in the radiation room and communicate to the radiation safety system controller that a person has been detected.

22 Claims, 4 Drawing Sheets

IDENTIFYING THE PRESENCE OF AN INDIVIDUAL NEAR MEDICAL RADIATION EMITTING EQUIPMENT

TECHNICAL FIELD

The present invention relates generally to radiation emitting medical instruments, and more specifically to a safety system for radiation emitting medical instruments.

BACKGROUND

Medical professionals commonly use radiation emitting medical instruments for medical diagnosis and treatment. More specifically, medical professionals may use radiation emitting medical devices for the treatment of cancer and medical imaging.

Medical imaging creates images of the human body for clinical purposes such as treatment of diseases, diagnosing diseases, and study of the human body. Many different types of medical imaging technology currently exists such as radiography (using x-rays), magnetic resonance imaging (MRI), tomography, ultrasound, and echocardiography. Some of these imaging technologies make use of radiation. While the radiation may be dangerous at high doses, controlled doses by medical imaging technology provides valuable pictures of the human body. These medical images may provide medical professions with a perspective of the body that cannot be seen by the naked eye, like bones structure.

The use of medical imaging is necessary for some medical treatments. Radiology, which is a common form of medical imaging, uses x-rays to produce an image of a part or all of the human body. X-rays, like visible light, are a type of radiation. X-rays have a much smaller wavelength (0.01 to 10 nanometers) and higher photo energies (100 eV to 100 keV) than visible light. The properties of x-rays provide both useful and harmful functions.

Because of the nature of some types of radiation, it can be harmful to cells in the human body. More specifically, radiation that carries enough energy to separate an electron from an atom or molecule is called ionizing radiation. Types of ionizing radiation include alpha rays, beta rays, gamma rays, and x-rays. If an ionizing ray interacts with a human cell, the cell may become ionized, which in turn damages or mutates the cell. On a more macro scale, extremely high doses of radiation can cause radiation burns and death. Some doses of radiation may cause cancer after exposure. Because of the risks for harm, unprotected exposure to ionizing radiation should be prevented.

Medical equipment that emits radiation may also be used for treatment of disease. Radiation therapy uses ionizing radiation for the treatment of cancer. By targeting ionizing radiation rays at cancer cells, tumors may be prevented from growing and in some cases may be reduced in size. Radiation therapy is useful in this situation because the dangerous rays are being targeted at harmful cancer cells. When applying radiation therapy, a radiologist must carefully select a location and a dosage of the applied radiation. Usually the location and dosage are electronically controlled for a more exact treatment of cancer. If radiation is not applied to the correct area of the body, the radiation may harm healthy cells instead of the cancerous cells.

While doctors control the amount of radiation exposure that a patient is subject to during a simple x-ray or an computed tomography (CT) scan, the radiation may still be dangerous. Doctors take affirmative steps to protect patients receiving an x-ray or CT scan, such as providing lead shielding, but protection from radiation is equally important for those who are not shielded, such as a radiologist performing the scan, nurses assisting in the scan, or family members of the patient providing moral support. So, measures should be taken to protect people other than the patient as well.

Generally, all people other than the patient should be a safe distance away from the radiation equipment and usually are outside of the room housing the radiation equipment. However, in some cases, a family member, who may be unshielded, may remain in the scanning room during the scan. Alternatively, a doctor or nurse may still be explaining the radiation procedure to the patient when a radiologist accidentally starts the scan. Many situations exist where an unshielded person other than the patient may remain in the treatment room and is exposed to dangerous radiation. These situations should be avoided at all costs because of the possibility of inducing cancer or other harm.

Currently, the only protective measure against unprotected radiation exposure in a medical treatment room is the diligence of the operator of the radiation equipment. While generally effective, the risk of an unprotected radiation exposure is too high to leave in the hands of just the operator. The operator has a lot of responsibility including checking that the radiation equipment is properly positioned, answering patient questions, providing radiation shielding (or other protective measures) to the patient, and also confirming that no unprotected people are proximate to the scanning equipment. With all these responsibilities, an operator may forget to do a head-count before activating the radiation equipment. Thus, to prevent unprotected exposure, the field of medicine needs a safety system to assure that only a protected patient is subject to radiation from the radiation equipment.

SUMMARY

The systems and methods described herein attempt to overcome the drawbacks discussed above by providing a radiation safety system connected to a radiation emitting apparatus that detects the number of people inside a room housing the radiation emitting apparatus. By taking a digital headcount, the radiation safety system is able prevent the radiation emitting apparatus from beginning the radiation emitting operation until all people who entered the room, other than the patient, have left the room.

The safety system may also be able to detect which people are in the room before beginning the radiation emitting operation. If the system determines that only the patient is in the room, the safety system allows the radiation emitting operation to commence. If a person other than the patient is detected in the room, the system will prevent the radiation emitting operation from beginning.

In the exemplary embodiments, radiation emitting functions of the radiation emitting apparatus are prevented if any unprotected people are within a distance, or in a room, where radiation may harmfully affect a person. Thus, the radiation safety system prevents radiation exposure for unprotected people.

In one embodiment, a radiation safety system comprises radiation emitting medical equipment; a radiation safety system controller connected to the radiation emitting medical equipment through a first communication means configured to determine a number of people within a radiation room housing the radiation emitting medical equipment and prevent the radiation emitting medical equipment from performing radiation emitting functions if the radiation safety system controller determines that more people than a maximum allowed number of people are presently in the radiation room;

and a scanner connected to the radiation safety controller through a second communication means configured to detect people in the radiation room and communicate to the radiation safety system controller that a person has been detected.

In another embodiment, a computer-implemented method for radiation safety comprises: detecting, by a scanner, whether a person is within a radiation room housing radiation emitting medical equipment; receiving, by a computer, a message from the scanner that a person has been detected; tracking, by a computer, the number of people within the radiation room based on a message from the scanner; receiving, by a computer, a request to perform a radiation emitting function of the radiation emitting medical equipment; determining, by a computer, whether the detected number of people in the radiation room is above a maximum number of people allowed in the radiation room; and preventing, by a computer, the radiation emitting medical equipment from emitting radiation if the detected number of people in the radiation room is above the maximum number of allowed people in the radiation room.

In yet another embodiment, a computer-implemented method for radiation safety comprises: detecting, by a scanner, the identity or characterization of a detected person within a radiation room housing radiation emitting medical equipment; receiving, by a computer, a message from the scanner indicating the identity or characterization of the detected person; receiving, by a computer, a request to perform a radiation emitting function of the radiation emitting medical equipment; determining, by a computer, whether the detected person is a patient; and preventing, by a computer, the radiation emitting medical equipment from performing the radiation emitting function if the detected person is not the patient.

Additional features and advantages of an embodiment will be set forth in the description which follows, and in part will be apparent from the description. The objectives and other advantages of the invention will be realized and attained by the structure particularly pointed out in the exemplary embodiments in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings constitute a part of this specification and illustrate an embodiment of the invention and together with the specification, explain the invention.

DETAILED DESCRIPTION

Reference will now be made in detail to the preferred embodiments, examples of which are illustrated in the accompanying drawings. The embodiments described above are intended to be exemplary. One skilled in the art recognizes that numerous alternative components and embodiments that may be substituted for the particular examples described herein and still fall within the scope of the invention.

Figure 1:
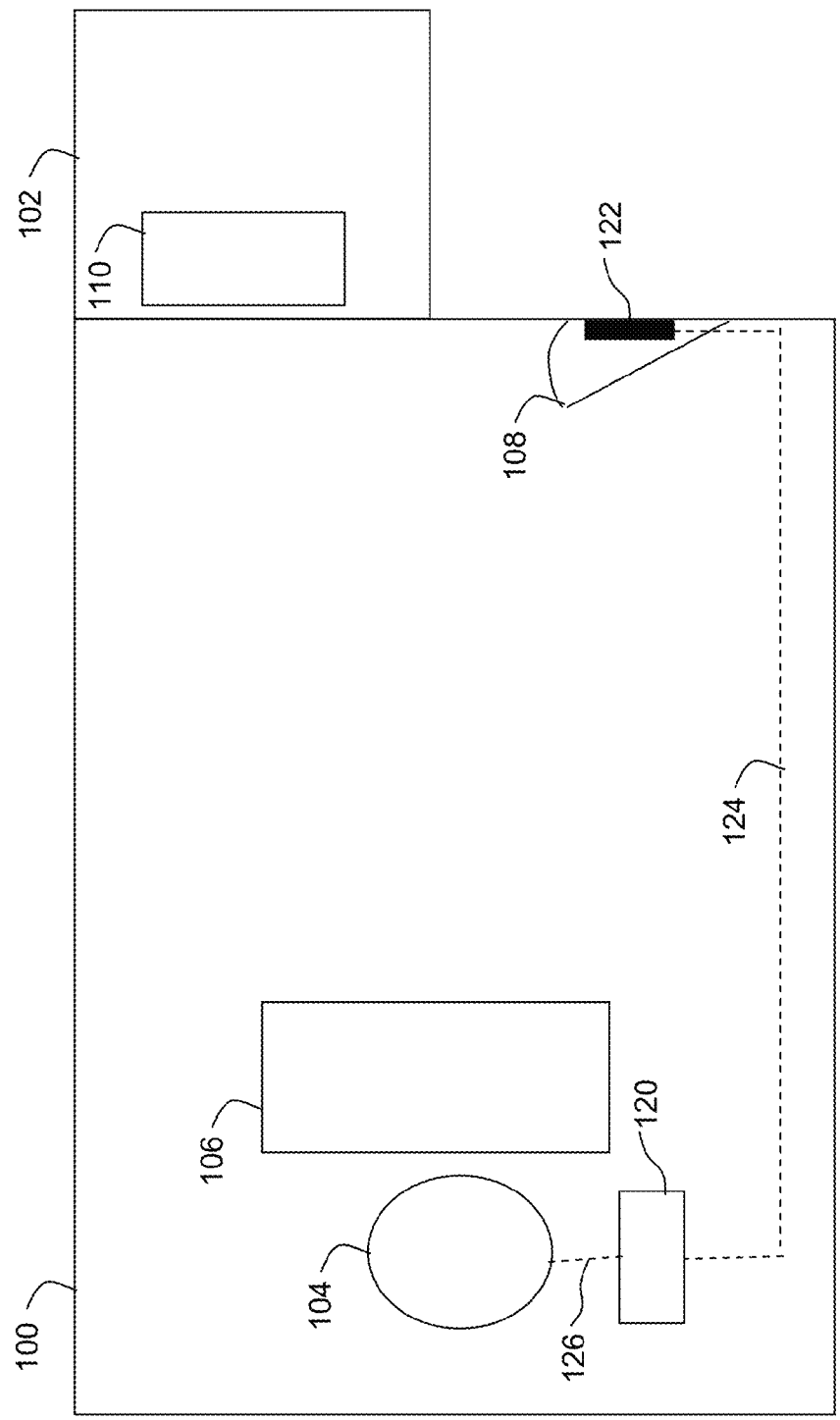
FIG. 1 illustrates a treatment room layout including a radiation safety system according to an exemplary embodiment.

Referring to FIG. 1, a medical treatment room layout including a radiation safety system according to the exemplary embodiments is illustrated. The medical treatment room may include a radiation room 100 and an operations room 102. The radiation room 100 includes radiation equipment 104, a patient bed 106, and a door 108. The radiation room 100 is the room in which the radiation equipment 104 emits radiation, which may be a piece of medical imaging equipment or a radiation therapy machine for the treatment of cancer. A wall may separate the radiation room 100 and the operation room 102. The radiation room 100 may be specially designed to prevent radiation from permeating through the walls of the radiation room 100. For example, relatively thick walls (e.g., about 6 to 12 inches) may surround the radiation room 100, or the walls of the radiation room 100 may comprise a material that attenuates radiation. The radiation room 100 may comprise other features, like orientation, lighting, a lack of windows, etc., specifically designed to attenuate the radiation from the radiation equipment 104.

An operator, such as a radiologist or an oncologist, may activate the radiation equipment 104 by interacting with controls 110 in the operations room 102. The controls 110 may control a position the radiation equipment 104, a dose of radiation from the radiation equipment 104, and also may display a patient's medical report. The radiation equipment 104 may have a number of different settings and functions, which are beyond the scope of the exemplary embodiments. Based on a thoughtful design of the radiation room 100, a person should be safe from the radiation emitted by the radiation equipment inside the operation room 102 even though the operations room 102 may be adjacent to the radiation room 100, as is illustrated in FIG. 1.

A patient may lay on the patient bed 106 during a medical procedure performed by the radiation equipment 104. During the medical procedure performed by the radiation equipment 104, the patient is subject to radiation. As a precaution, medical professionals provide shielding to protect the patient from radiation. The shielding provided to the patient may comprise lead. The shielding may protect areas of the patient's body which are not targeted by the radiation equipment 104. However, other people, such as the radiologist, oncologist, or family members of the patient, should also be protected. The best and easiest way to protect people other than the patient is to move the other people away from the radiation equipment 104, and preferably, out of the radiation room 100.

To protect people other than the patient from radiation exposure, a radiation safety system controller 120 performs radiation safety operations and connects to the radiation equipment 104. To assist the radiation safety system controller 120, a scanner 122 connects to the radiation safety system controller 120. A first connection 124 connects the scanner 122 to the radiation safety system controller 120, and a second connection 126 connects the radiation safety system controller 120 to the radiation equipment 104. The first and second connection 124, 126 may connect electronic equipment together, such as a wired means or wireless means. The first and second connection 124, 126 may be a serial connection, universal serial bus connection, fiber optic cable, or any other type of wired connection means. Alternatively, the first and second connection 124, 126 may use a wireless communication connection following a wireless communication standard, such as 802.11 standards, Bluetooth 802.15 standards, or infrared data association standard.

Figure 2:
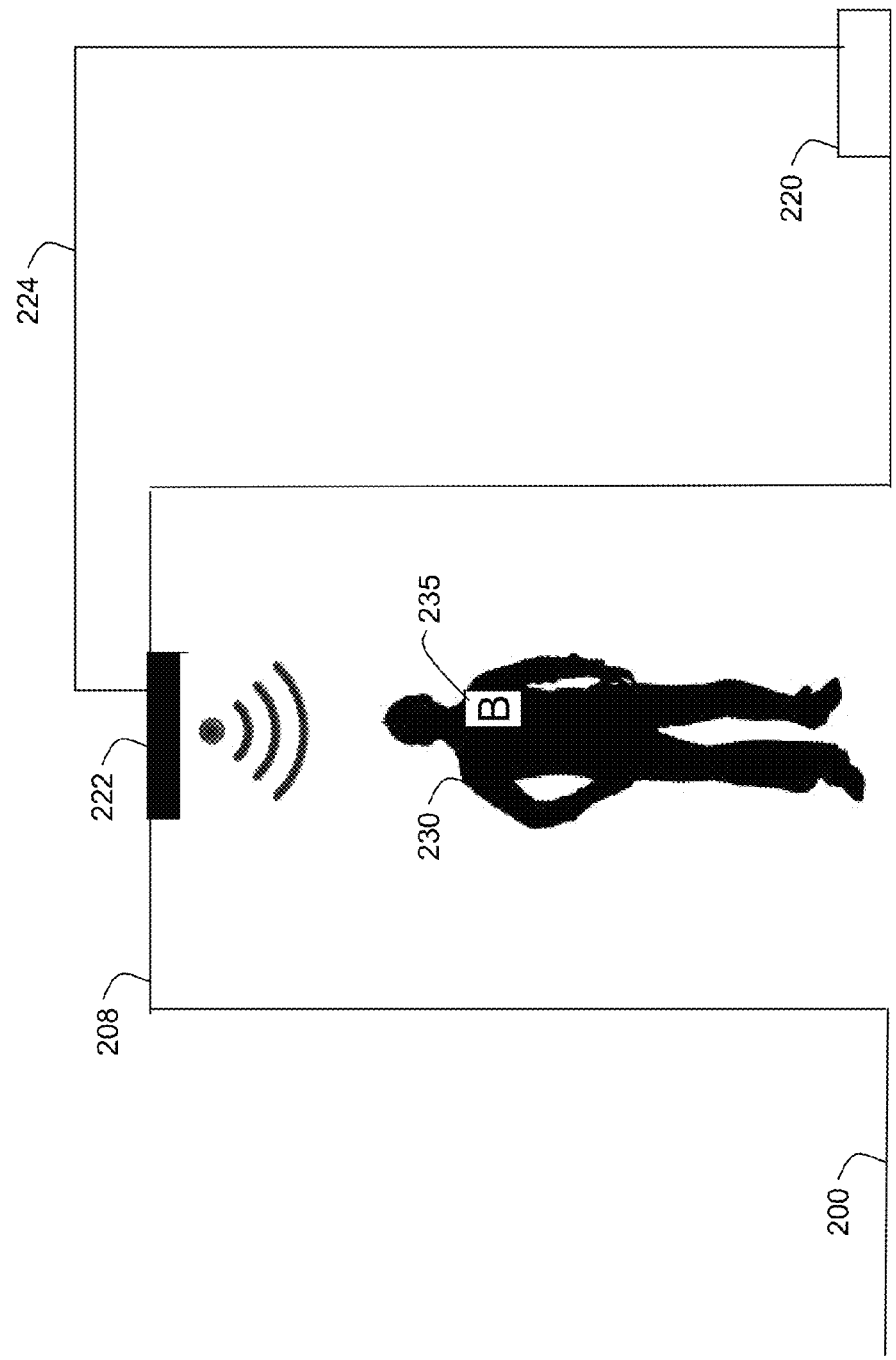
FIG. 2 illustrates a door system that scans people entering and leaving through the door of a treatment room according to an exemplary embodiment.

In a first embodiment, the scanner 122 may be an RFID scanner that detects when an RFID tag passes through the door 108. FIG. 2 illustrates an RFID scanner for detection of RFID tags that pass through a door, which may be implemented according to the layout illustrated in FIG. 1.

Referring now to FIG. 2, a person 230 wears an RFID badge 235. The scanner 222 detects whether the person 230 has entered the radiation room 200 through the door 208. When the person 230 enters the room, the scanner 222 sends a message to the radiation safety system controller 220 through the first connection means 224 notifying the radiation safety system controller 220 that a person has entered the room. The radiation safety system controller 220 keeps a digital headcount of the people who are present in the room 200 by storing a digital code representing each person 230 present in the room 200 in a computer readable storage device, such as memory. The radiation safety system controller 220 may include the computer readable storage device, and may read data from and write data to the computer readable storage device using a digital processor.

Whenever the scanner 222 detects an RFID badge 235 passing under the threshold of the door 208, the scanner 222 sends an identification code specifically assigned to the RFID badge 235 to the radiation safety system controller 220. For example, the identification code of the RFID badge 235 may include the person's 230 name, position, status, or other identifier. This may be the case for every employee in a medical facility that includes the radiation room 200. As an more specific example, if the person 235 is Doctor A, Doctor A's RFID badge 235 identifies him as Doctor A to the radiation safety system controller 220. When the scanner 222 reads the identification code that identifies Doctor A, the scanner 222 sends Doctor A's identification code to the radiation safety system controller 220, and the radiation safety system controller 220 determines that Doctor A is presently within the radiation room 200. The radiation safety system controller 220 stores the identification codes representing all the people who enter the room 200 in the computer readable storage device as a method of keeping track of all people who enter the room 200.

If, after the radiation safety system controller 220 determined that Doctor A entered the radiation room 200, the scanner 222 again detects Doctor A's RFID badge 235, and the scanner 222 sends the identification code identifying Doctor A to the radiation safety system controller 220. Upon receiving the identification code for Doctor A again, the radiation safety system controller 220 notices that Doctor A was previously identified as inside of the radiation room 200 by referencing the computer readable storage device. When the radiation safety system controller 220 receives the identification code of a person 230 previously determined to be inside the room 200, the radiation safety system controller 220 determines that the person 230 is leaving the radiation room 200. In the case of Doctor A, leaving through the door 208, the radiation safety system controller 220 determines that Doctor A is no longer in the room and no longer at any risk of radiation exposure. In one embodiment, the radiation safety system controller 220 may erase the Doctor A's identification code from the computer readable storage device when Doctor A leaves the room 200 as a way of representing that Doctor A is no longer present in the radiation room 200.

In some embodiments, which are described in more detail below, the scanner 222 detects the presence of RFID badges 235 anywhere inside the room 200. When the scanner detects an RFID badge 235, the radiation safety system controller 220 determines that the person 230 is in the room 200. If the presence of an RFID badge 235 is not detected by the scanner 222, the radiation safety system determines that the person 230 is not present within the room 200. A system of this nature may be used if the RFID scanner 222 is only able to detect the presence of RFID transponders inside of the room 200. So, if the scanner 222 detects the RFID badge 235 for Doctor A, the radiation safety system controller 220 determines that Doctor A is inside the room 200.

RFID badges 235 identification codes may be general or specific. For example, the identification code may represent a category of people, such as "patients," "doctors," "employees," or "guests." Alternatively, the RFID badge 235 identification code may include a name of the person 230, such as in the example of Doctor A. Of course, the radiation scanning system 220 may implement a combination of these two identification code techniques, such as by identifying all medical employees and patients by name, while issuing general "guest" badges 235 to friends and family members.

Referring to FIGS. 1 and 2, the radiation safety system controller 120 prevents activation of the radiation equipment 104 if a person who is not supposed to be exposed to radiation is inside of the radiation room 100. Because certain patients are supposed to be exposed to radiation, the radiation safety system controller 120 must determine that the patient is inside the radiation room 100, and also must determine that all people other than the patient are not in the radiation room 100.

The radiation safety system controller 120 may prevent the activation of radiation emitting features of the radiation equipment 104 by a counting method. The counting method may be used in a less sophisticated radiation safety system where the radiation safety system controller 120 is unaware which RFID badge 235 is the patient's. For example, the radiation safety system controller 120 may count the number of times the scanner 122 reads an RFID badge 235. The radiation safety system controller 120 may uniquely count each identification code detected by the scanner 122. Thus, every time the scanner 122 detects an RFID badge 235, the count for that specific RFID badge 235 is increased by one. It should be noted that, in the counting method, the scanner 122 has a relatively small scanning radius such that the scanner 122 detects RFID badges 235 immediately under or very close to the door 108. Accordingly, if the count of any given RFID badge 235 identification code is an even number, the radiation safety system controller 120 assumes that the person represented by the identification code is not in the room. If the count of any given RFID badge 235 identification code is an odd number, the radiation safety system controller 120 assumes that the person associated with that RFID badge 235 is present within the room. Next, the radiation safety system controller 120 determines if only one identification code has an odd number, and the radiation safety system controller 120 allows the radiation equipment 104 to emit radiation if only one identification code has an odd number. While relatively simple, this counting method may still cause safety concerns. For example, if a nurse is the only person in the room 100 (and thus the only RFID badge 235 identification code with an odd number) to simply clean up the room 100, an accidental activation of the radiation equipment 104 may still expose the nurse to radiation.

Thus, a preferred system 120 is able to at least identify a patient from among all of the RFID badges 235 that enter the room 100, which may be called a specific identity method. Most RFID badges 235 include integrated circuits having plenty of data storage to save identity information. For example, the RFID badge 235 may be programmed with the name of the patient. By identifying the patient by name, the radiation safety system controller 120 may connect to patient medical records, such as through the ARIA® oncology information system that allows the radiation equipment 104 operator to confirm that the correct patient in the radiation room 100. According to the specific identity method, the radiation safety system controller 120 performs an additional procedural step verifying that only the patient is inside the room 100.

The RFID badge 235 may also be programmed with a medical procedure instead of an identity of the patient wearing the badge 235. For example, a "CT Scan" badge 235 may be issued to all patient who are to receive a CT scan. Another category of badge 235 may be a "radiation therapy" badge 235. The radiation safety system controller 120 may first verify that only one person is in the room 100 and subsequently verify that the person in the room 100 has a badge 235 corresponding to the medical procedure performed by the radiation equipment 104. For example, in a radiation room 100 where the radiation equipment 104 is a CT scanner, the radiation safety system controller 120 may check that the badge 235 of the person 230 in the room is a "CT scan" badge 235. While it is probably rare that a patient stumbles into the wrong medical room and receives an incorrect procedure, more generic badges 235 of this nature could be reused without the need to reprogram the badge 235 for every new patient.

More advanced RFID systems may be able to detect the position of an RFID badge 235 in the room 100. In such an advanced system, the scanner 122 sends the exact position of all people in the room 100 to the radiation safety system controller 120. If the radiation safety system controller 120 determines that only one person is in the room 100, and that the person in the room is the patient, the radiation safety system controller 120 allows the radiation emitting functions of the radiation equipment 104. The radiation safety system controller 120 may further check if the location of the person in the room 100 is proximate to the patient bed 106 as a way to check that the patient is ready for the radiation emitting procedure. Advanced RFID systems may require active RFID transponders that have a power source, like a battery included. Such active RFID transponders may be more expensive.

The RFID badge 235 includes an RFID transponder. The RFID transponder may be an active or passive RFID transponder. As discussed above, if the position from the scanner 122 is necessary as part of the process to detect people in the radiation room 100, an active RFID transponder may be implemented. Passive RFID transponders do not need an internal power supply because they are powered by the electromagnetic signal supplied by the scanner 122. Passive RFID transponders are generally less expensive than active RFID transponders.

If a simpler RFID system is adopted, which includes passive RFID transponders, the range of the scanner 222 may become important. In a system that detects whenever people pass through the door 208, the scanner 222 should only read the RFID badge 235 when the person 230 enters or the leaves the room, not whenever a person 230 is near the door 208. For example, the scanner 222 should not obtain a false reading that the person 230 is leaving just because the person 230 approached the door 208 to interact with something near the door 208, such as a light switch. Thus, the position, range, and scanning direction of the scanner 222 becomes very important to prevent false readings.

To combat false readings, the scanner 222 may have a very limited range, for example two to four feet. Depending where the scanner 222 is placed, the limited range may prevent false scanner 222 readings. As illustrated in FIG. 2, the scanner 222 is placed above the center of the door 208. Assuming the door 208 is about seven or eight feet high, if the scanner had a range of four feet, it could detect a badge 235 worn on the breast of an person 230 of average height only when the badge 235 is directly below the scanner 222. However, not all people wear badges 235 at their breast, and some people wear a badge 235 at their waist. Also, some people, such as young children, may be too short to be recognized by the scanner 222 if the range is too limited. Of course, the range of the scanner 222 may be calibrated according to the room 200 or the typical client height. For example, the scanner 222 may have a different range, or be positioned differently for a pediatrician's office where a common patient is a small child.

Positioning two scanners, one inside the room 200 and one outside the room 200, may also combat false readings. Using the two scanner 222 configuration, the radiation safety system controller 220 determines that a person has entered the room 200 if the same RFID badge 235 identification code has been read at both the scanner 222 outside the room 200 and subsequently at the scanner 222 inside the room 200. Conversely, the radiation safety system controller 220 determines that a person has left the room 200 if the same RFID badge 235 identification code has been read at both the scanner 222 inside the room 200 and subsequently at the scanner 222 outside the room 200. Using the two scanner 222 configuration, both ranges of the scanners 222 may be increased to the height of a ceiling, such that the two ranges do not overlap.

Another way to combat false readings is to make use of the properties of the room 200. In many radiation rooms 200, the walls may be quite thick to prevent any dangerous radiation from passing into another room. Walls of this thickness may also prevent radio signals, which are used by RFID scanners 222, from permeating through the walls. Thus, as long as the scanner 222 is positioned within the room 200, the scanner 222 may have any range and can detect RFID transponders only within the room 200 because the scanner 222 cannot detect RFID transponders outside of the room 200. Of course, any doors 208 or windows of the room 200 also must have radio wave deflecting properties. Also, if the door 208 was open, the scanner 222 may be able to detect RFID transponders outside of the room 200 located relatively close to the opened door 208. However, the opened door 208 problem may actually be an additional safety feature because the radiation equipment 104 should not be operated when the door 208 is open.

If the walls and doors 208 of the room 200 are capable of preventing radio waves from leaving the room 200, the scanner 222 may have a range sufficient to read an RFID transponder anywhere in the room 200. Thus, the RFID scanner 222 detects the presence of people 230, and the radiation safety system controller 220 does not need to perform the counting method discussed above. So, if a person other than the patient is detected by the scanner 222, the radiation safety system controller 220 prevents the radiation equipment 104 from emitting radiation. The scanner 222 according to this embodiment may be placed anywhere in the room 200. Preferably, the scanner 222 resides on the ceiling in the middle of the room so that the range of the scanner may be as short as possible, and thus providing cost and energy savings.

In yet another way to combat false positives, the scanner 222 may have a directional antenna to send radio waves in specific directions. For example, the range of the scanner 222 may be the entire height of the door 208, but by using a directional antenna, the direction antenna sends radio waves directly downward from the scanner 222, if the scanner 222 is placed at the top of the door 208 frame. The directional antenna may allow the scanner 222 to only detect RFID transponders that are directly under the door 208 frame. The radiation safety system controller 220 may implement the counting method to track the entry and exit of people 230 into the room 200 using a directional antenna.

While the radiation safety system controller 120 has been described as preventing radiation equipment 104 from emitting radiation if a person other than the patient is in the room 100, the radiation safety system controller 120 may be programmed to allow the presence of other people in the radiation room 100 if the other people are supposed to be in the room 100. For example, if a small child receives an x-ray, a properly shielded parent may stay with the child to alleviate the child's fears of the procedure. In a situation such as this, the radiation equipment 104 operator may override the normal functions of the radiation safety system controller 120, which prevents radiation emission if a person other than the patient is in the room 100, and command the radiation safety system controller 120 to expect the patient and a guest to remain in the room during the operation of the radiation equipment 104. In the parent/child x-ray example given above, the radiation safety system controller 120 may verify that two people are in the room 100, and the two people in the room have a "patient" badge 230 and a "guest" badge 230 before allowing the radiation equipment 104 from emitting radiation.

If the radiation safety system controller 120 detects that no people are in the room, and an operator attempts to activate the radiation equipment 104, the radiation safety system controller 120 may also prevent activation of the radiation equipment 120. This feature may be a power saving feature. Alternatively, an operator may be able to activate a test mode, which may allow the radiation equipment 104 to operate when no people are present in the room 100. In yet another embodiment, the radiation safety system controller 120 may always allow the radiation equipment 104 to perform radiation emitting functions when no people are in the room 100

Figure 3:
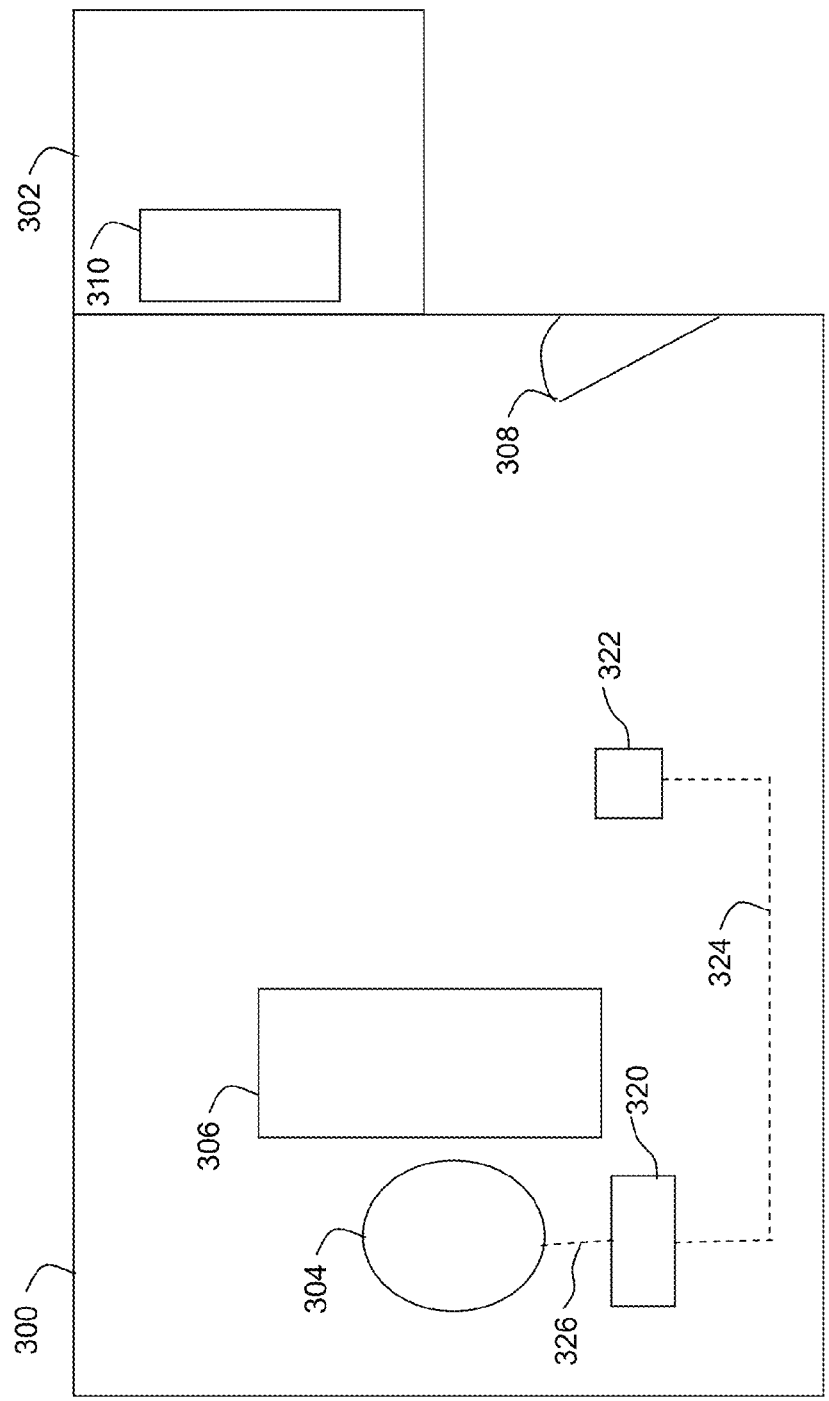
FIG. 3 illustrates another treatment room layout including a radiation safety system according to an exemplary embodiment.

FIG. 3 illustrates another treatment room layout including a radiation safety system controller according to the exemplary embodiments. In the treatment room layout of FIG. 3, thermal imaging detects the presence of people in the treatment room. As shown in FIG. 3, the medical treatment room may include a radiation room 300, and an operations room 302. The radiation room 300 includes radiation equipment 304, a patient bed 306, and a door 308. The radiation room 300 is the room in which radiation is emitted from the radiation equipment 304. A wall may separate the radiation room 300 and the operation room 302 to protect an operator of the radiation equipment 304.

A patient may lay on the patient bed 306 during the medical procedure. During the medical procedure, the patient is subject to radiation. However, other people should not be subject to the radiation. Accordingly, the patient may have a badge with a particular identifier or may not use a badge.

To protect people other than the patient from radiation exposure, a radiation safety system controller 320 performs radiation safety operations and connects to the radiation equipment 304. To assist the radiation safety system controller 320, a scanner 322 connects to the radiation safety system controller 320. A first connection means 324 connects the scanner 322 to the radiation safety system controller 320, and a second connection means 326 connects the radiation safety system controller 320 to the radiation equipment 304. The first and second connection means 324, 326 may be any means of connecting electronic equipment together. The radiation safety system controller 320 and the connection means 324, 326 may be the similar to the radiation safety system controller 120 and connection means 124, 126 described in FIG. 1.

As mentioned above, the scanner 322 is a thermal imaging scanner. Thermal imaging may require the use of multiple scanners 322, but one scanner 322 will be described for illustration purposes. The thermal imaging scanner 322 is capable of detecting a person by sensing their body heat.

Using the thermal imaging scanner 322, the radiation safety system controller 320 may determine how many people are inside the radiation room 300. However, the thermal imaging scanner 322 may not be able to determine the identity of detected people simply by body heat signatures. However, thermal imaging scanners 322 may be able to determine if the person is proximate to the patient bed 306, and further may be able to determine if a detected body heat signature is laying on the patient bed 306. As an additional safety check, the radiation safety system controller 320 may first check if only one person is in the radiation room 300, and subsequently check if the one person is proximate to or lying on the patient bed 306. Some radiation rooms 300 may have moving patient beds 306. Moving patient beds 306 may move a person on the patient bed 306 at different angles and also to different locations within the radiation room 300. If a moving patient bed 306 is included, the location and angle of the patient bed 306 may be reported to the radiation safety system controller 320 so that the it can make check the location and orientation of the person's body heat signature against the reported location and angle of the patient bed 306. Such a report of the location and angle of the patient bed 306 may be provided to the radiation safety system controller 320 if the patient bed 306 is connected to a electro-mechanical movement system.

While RFID and thermal imaging have been described as exemplary embodiments of the scanner 122, 322, any people counting technology may be included in the radiation safety system controller 120, 320 in the scope of the exemplary embodiments. Such people counters include infrared beams, computer vision, or pressure sensitive mats.

Figure 4:
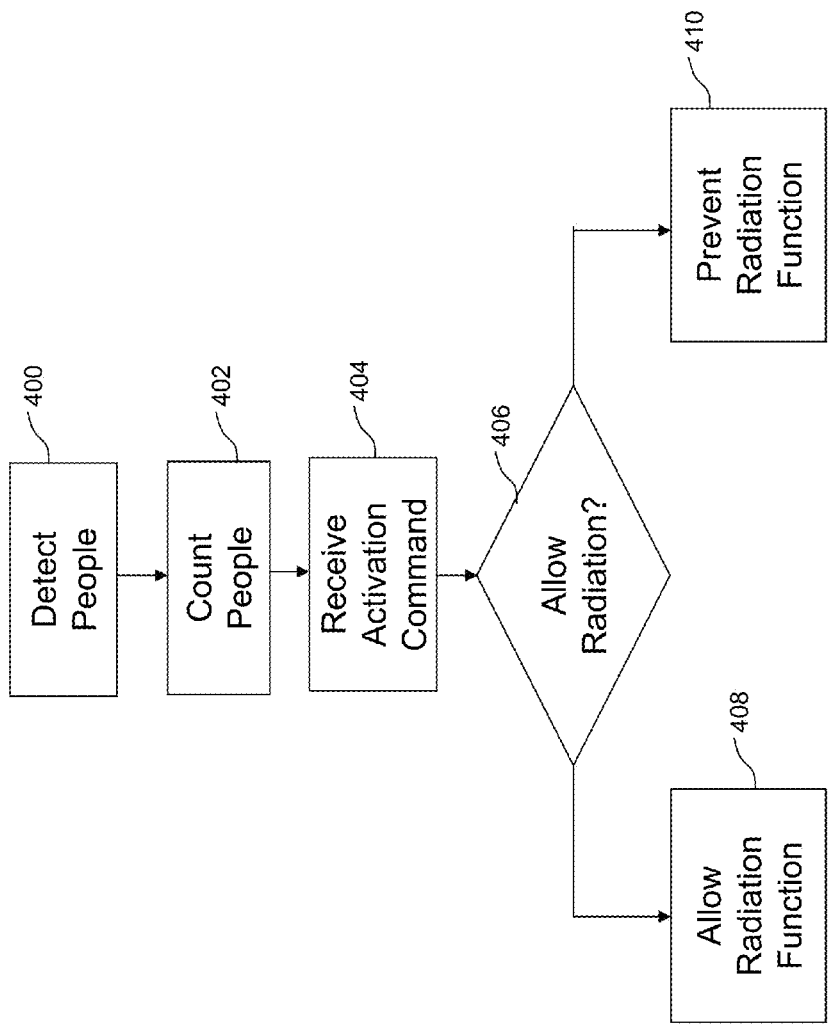
FIG. 4 illustrates a method of implementing a radiation safety system connected to radiation equipment according to an exemplary embodiment.

Referring to FIG. 4, an exemplary method performed by the radiation safety system controller is illustrated. The method begins in step 400, where the radiation safety system controller detects whether people have entered or left the room. In some embodiments, the radiation safety system controller may detect if people are presently in the room. The people detection step 400 may be performed by any people counter, such as the RFID system or thermal imaging system described above. The people detection step 400 is conducted continuously throughout the operation of the radiation safety system controller. Whenever a person is detected, the radiation safety system controller stores the detected person in a computer readable storage device. The counting system described above may be one instance of the way the computer readable storage device is used to account for the presence of people in the radiation room. The computer readable storage device may move identification codes of people in the room to a specific block of memory, or by raising a flag for each identification code corresponding to a person in the radiation room.

Whatever the manner by which the radiation safety system controller detects people, the radiation safety system controller is configured to count the number of people presently in the radiation room, which is illustrated in step 402. By counting the number of identification codes, heat signatures, or other manner of identifying individuals, the radiation safety system controller determines how many people are in the radiation room. The count of the number of people in the radiation room may also include a determination of whether the patient is in the radiation room, which may be determined by looking at individual identification codes or by looking at position and orientation data describing a state a heat signature (i.e. laying on patient bed or not).

When a command is sent from the radiation equipment controls to activate the radiation emitting functions of the radiation equipment in step 404, the radiation safety system controller decides whether to allow the radiation emitting function of the radiation equipment in step 406. If only the patient is in the radiation room, the radiation safety system controller allows the radiation equipment to emit radiation in step 408. If the patient is not the only person in the room, the radiation safety system controller prevents the radiation equipment from emitting radiation in step 410.

The exemplary embodiments can include one or more computer programs that embody the functions described herein and illustrated in the appended flow charts. However, it should be apparent that there could be many different ways of implementing aspects of the exemplary embodiments in computer programming, and these aspects should not be construed as limited to one set of computer instructions. Further, those skilled in the art will appreciate that one or more acts described herein may be performed by hardware, software, or a combination thereof, as may be embodied in one or more computing systems.

The functionality described herein can be implemented by numerous modules or components that can perform one or multiple functions. Each module or component can be executed by a computer, such as a server, having a non-transitory computer-readable device and processor. In one alternative, multiple computers may be necessary to implement the functionality of one module or component.

Unless specifically stated otherwise as apparent from the following discussion, it is appreciated that throughout the description, discussions utilizing terms such as "processing" or "computing" or "calculating" or "determining" or "displaying" or "generating" or "synchronizing" or "outputting" or the like, can refer to the action and processes of a data processing system, or similar electronic device, that manipulates and transforms data represented as physical (electronic) quantities within the system's registers and memories into other data similarly represented as physical quantities within the system's memories or registers or other such information storage, transmission or display devices.

The exemplary embodiments can relate to an apparatus for performing one or more of the functions described herein. This apparatus may be specially constructed for the required purposes, or it may comprise a general purpose computer selectively activated or reconfigured by a computer program stored in the computer. Such a computer program may be stored in a machine (e.g. computer) readable storage device, such as, but is not limited to, any type of disk including floppy disks, optical disks, CD-ROMs and magnetic-optical disks, read only memories (ROMs), random access memories (RAMs) erasable programmable ROMs (EPROMs), electrically erasable programmable ROMs (EEPROMs), magnetic or optical cards, or any type of media suitable for storing electronic instructions, and each coupled to a bus.

The exemplary embodiments described herein are described as software executed on at least one server, though it is understood that embodiments can be configured in other ways and retain functionality. The embodiments can be implemented on known devices such as a personal computer, a special purpose computer, cellular telephone, personal digital assistant ("PDA"), a digital camera, a digital tablet, an electronic gaming system, a programmed microprocessor or microcontroller and peripheral integrated circuit element(s), and ASIC or other integrated circuit, a digital signal processor, a hard-wired electronic or logic circuit such as a discrete element circuit, a programmable logic device such as a PLD, PLA, FPGA, PAL, or the like. In general, any device capable of implementing the processes described herein can be used to implement the systems and techniques according to this invention.

It is to be appreciated that the various components of the technology can be located at distant portions of a distributed network and/or the Internet, or within a dedicated secure, unsecured and/or encrypted system. Thus, it should be appreciated that the components of the system can be combined into one or more devices or co-located on a particular node of a distributed network, such as a telecommunications network. As will be appreciated from the description, and for reasons of computational efficiency, the components of the system can be arranged at any location within a distributed network without affecting the operation of the system. Moreover, the components could be embedded in a dedicated machine.

Furthermore, it should be appreciated that the various links connecting the elements can be wired or wireless links, or any combination thereof, or any other known or later developed element(s) that is capable of supplying and/or communicating data to and from the connected elements. The term module as used herein can refer to any known or later developed hardware, software, firmware, or combination thereof that is capable of performing the functionality associated with that element. The terms determine, calculate and compute, and variations thereof, as used herein are used interchangeably and include any type of methodology, process, mathematical operation or technique.

The embodiments described above are intended to be exemplary. One skilled in the art recognizes that numerous alternative components and embodiments that may be substituted for the particular examples described herein and still fall within the scope of the invention.

What is claimed is:

1. A radiation safety system comprising:
   radiation emitting medical equipment;
   a radiation safety system controller connected to the radiation emitting medical equipment through a first communication means configured to determine a number of people within a radiation room housing the radiation emitting medical equipment and prevent the radiation emitting medical equipment from performing radiation emitting functions if the radiation safety system controller determines that more people than a maximum allowed number of people are presently in the radiation room; and
   a scanner connected to the radiation safety controller through a second communication means configured to detect people in the radiation room and communicate to the radiation safety system controller that a person has been detected,
   wherein the radiation safety system controller prevents the radiation emitting medical equipment from performing a radiation emitting function if the radiation safety system controller determines that no people other than a patient are presently in the radiation room.

2. The radiation safety system of claim 1, wherein the scanner is an RFID scanner configured to detect an RFID transponder having an identification code included in a badge.

3. The radiation safety system of claim 2, wherein the identification code characterizes a person wearing the badge into one of a plurality of categories.

4. The radiation safety system of claim 3, wherein the categories include patient, employee, and guest.

5. The radiation safety system of claim 4, wherein the radiation safety system controller is further configured to verify that a detected RFID transponder has an identification code that corresponds to the "patient" category before allowing the radiation emitting medical equipment to perform a radiation emitting function.

6. The radiation safety system of claim 2, wherein the identification code identifies a name of a person wearing the badge.

7. The radiation safety system of claim 6, wherein the radiation safety system controller is further configured to verify that the name stored in a detected RFID transponder matches a patient's name stored in a medical record before allowing the radiation emitting medical equipment to perform a radiation emitting function.

8. The radiation safety system of claim 3, wherein the radiation safety system controller is further configured to verify that a detected RFID transponder has an identification code that corresponds to a medical procedure category matching the medical procedure performed by the radiation emitting medical equipment before allowing the radiation emitting medical equipment to perform a radiation emitting function.

9. The radiation safety system of claim 2, wherein the scanner detects the RFID transponder when the RFID transponder passes through a door of the radiation room.

10. The radiation safety system of claim 9, wherein the radiation safety system controller maintains a count for each detected identification code such that:
   if the count of the detected identification code is an even number, the radiation safety system controller determines that a person wearing the badge is outside the radiation room; and
   if the count of the RFID badge identification code is an odd number, the radiation safety system controller determines that a person wearing the badge is inside the radiation room.

11. The radiation safety system of claim 9, wherein the scanner includes a directional antenna.

12. The radiation safety system of claim 1, wherein the scanner comprises a first RFID scanner positioned inside the radiation room and a second RFID scanner positioned outside of the radiation room, such that a range of the first RFID scanner and a range of the second RFID scanner do not overlap.

13. The radiation safety system of claim 12, wherein the radiation safety system controller determines that a person has entered the radiation room if it receives a message from the second RFID scanner identifying a first RFID badge identification code and subsequently receives a message from the first RFID scanner identifying the first RFID badge identification code, and the radiation safety system controller determines that a person has left the radiation room if it receives a message from the first RFID scanner identifying the first RFID badge identification code and subsequently receives a message from the second RFID scanner identifying the first RFID badge identification code.

14. The radiation safety system of claim 1, wherein the scanner is a thermal imaging sensor configured to detect body heat signatures.

15. The radiation safety system of claim 14, wherein the radiation safety system controller is further configured to determine if a detected body heat signature is proximate to a patient bed.

16. The radiation safety system of claim 15, wherein the radiation safety system controller receives position and orientation data for the patient bed from a patient bed movement system to determine if the detected body heat signature is proximate to the patient bed.

17. The radiation safety system of claim 1, wherein when the scanner communicates to the radiation safety system controller that a person has been detected, the radiation safety system controller accesses a computer readable storage device.

18. A computer-implemented method for radiation safety comprising:
   detecting, by a scanner, the identity or characterization of a detected person within a radiation room housing radiation emitting medical equipment;
   receiving, by a computer, a message from the scanner indicating the identity or characterization of the detected person;
   receiving, by the computer, a request to perform a radiation emitting function of the radiation emitting medical equipment;
   determining, by the computer, whether the detected person is a patient; and
   preventing, by the computer, the radiation emitting medical equipment from performing the radiation emitting function if the detected person is not the patient.

19. The method of claim 18, wherein the scanner is an RFID scanner.

20. The method of claim 18, wherein the detected person is determined to be the patient if an RFID badge worn by the detected person corresponds to the patient.

21. The method of claim 18, wherein the scanner is a thermal imaging scanner configured to detect body heat signatures.

22. The method of claim 18, wherein the detected person is determined to be the patient if a body heat signature is proximate to a patient bed.

* * * * *